United States Patent
Shih

(10) Patent No.: US 7,732,332 B2
(45) Date of Patent: Jun. 8, 2010

(54) CHEMICAL MECHANICAL POLISHING METHOD WITH INSPECTION PRE AND POST PROCESSING

(75) Inventor: Hui-Shen Shih, Changhua Hsien (TW)

(73) Assignee: United Microelectronics Corp., Hsinchu (TW)

( * ) Notice: Subject to any disclaimer, the term of this patent is extended or adjusted under 35 U.S.C. 154(b) by 654 days.

(21) Appl. No.: 11/308,184

(22) Filed: Mar. 10, 2006

(65) Prior Publication Data

US 2007/0212881 A1    Sep. 13, 2007

(51) Int. Cl.
G01N 21/00 (2006.01)
H01L 21/302 (2006.01)

(52) U.S. Cl. ............... 438/691; 257/E21.304; 356/237.2

(58) Field of Classification Search .............. 356/237.2; 438/691; 257/E21.304
See application file for complete search history.

(56) References Cited

U.S. PATENT DOCUMENTS

2002/0107155 A1* 8/2002 Miller et al. ................. 510/108
2007/0122921 A1* 5/2007 Shanmugasundram et al. ... 438/14
2007/0281587 A1* 12/2007 Wiswesser et al. ............. 451/8

FOREIGN PATENT DOCUMENTS

EP    1017090 A1 * 7/2000

* cited by examiner

Primary Examiner—Matthew Smith
Assistant Examiner—Walter H Swanson
(74) Attorney, Agent, or Firm—Jianq Chyun IP Office

(57) ABSTRACT

The invention is directed to a chemical mechanical polishing process. The chemical mechanical polishing process comprises steps of providing a wafer disposed at a wafer handling region of a chemical mechanical polishing apparatus and then moving the wafer into a buffer region of the chemical mechanical polishing apparatus. A first detecting process is performed for obtaining a pre-polishing condition of the wafer by using a detector in the buffer region and the wafer is moved into a chemical mechanical polishing region and performing a chemical mechanical process. A second detecting process is performed, in the buffer region, for obtaining a post-polishing condition of the wafer by using the detector of the buffer region.

8 Claims, 2 Drawing Sheets

CHEMICAL MECHANICAL POLISHING METHOD WITH INSPECTION PRE AND POST PROCESSING

BACKGROUND OF THE INVENTION

1. Field of Invention

The present invention relates to a chemical mechanical polishing apparatus and an operating method thereof. More particularly, the present invention relates to a chemical mechanical polishing apparatus with a detector and an operating method thereof.

2. Description of Related Art

With the highly integration of the integrated circuit device, the size of the device is decreased and the number of the interconnects for the device is increased. Currently, when the devices, such as the diodes and transistors, are formed on the substrate, an insulating material layer is deposited on the integrated circuit device and then the insulating material layer is defined to form contact windows or vias. Finally, a conductive material is filled in the contact windows or vias to form vertical interconnections.

Because some of the conductive material cannot fully fill up the contact windows or vias, general technology for filling the contact windows or the vias is to deposit a tungsten layer over the insulating material layer to fill up the contact windows and the vias and then the overflow portion of the tungsten material is removed. The overflow portion of the tungsten material over the insulating material layer can be removed by using etching back process or chemical mechanical polishing process.

Since there is no interaction between the tungsten and the insulating material, the adhesion between the tungsten and the insulating material is poor. Hence, the tungsten peeling phenomenon happens easily. When the wafer with tungsten peeling surface is disregarded for a long time or is rinsed, the tungsten peeling spot will expand to be an entirely peeling situation. Currently, there is no detector assembled on the chemical mechanical polishing apparatus to inspect the peeling phenomenon or other defect on the wafer surface. Therefore, the only way to inspect the wafer surface condition is manual detection. However, the manual detection is not only inefficient but also imprecise. Once the wafer with a peeling surface is moved into a chemical mechanical polishing apparatus, it is possible to lead to the contamination and damage of the apparatus and the damage of the wafer. Accordingly, the cost is seriously wasted and the process efficiency and yield is decreased.

SUMMARY OF THE INVENTION

Accordingly, at least one objective of the present invention is to provide a chemical mechanical polishing process capable of preventing the chemical mechanical polishing apparatus from being contaminated by the wafer with peeling phenomenon thereon.

At least another objective of the present invention is to provide a chemical mechanical polishing apparatus capable of inspecting the wafer surface to insure whether there is peeling phenomenon or other defects on the wafer surface before the chemical mechanical polishing process is performed on the wafer.

To achieve these and other advantages and in accordance with the purpose of the invention, as embodied and broadly described herein, the invention provides a chemical mechanical polishing process. The chemical mechanical polishing process comprises steps of providing a wafer disposed at a wafer handling region of a chemical mechanical polishing apparatus and then moving the wafer into a buffer region of the chemical mechanical polishing apparatus. A first detecting process is performed for obtaining a pre-polishing condition of the wafer by using a detector in the buffer region and the wafer is moved into a chemical mechanical polishing region and performing a chemical mechanical process. A second detecting process is performed, in the buffer region, for obtaining a post-polishing condition of the wafer by using the detector of the buffer region.

According to the chemical mechanical polishing process of the embodiment of the present invention, the detector includes an optical detector.

According to the chemical mechanical polishing process of the embodiment of the present invention, the optical detector includes a laser detector and an infrared detector.

According to the chemical mechanical polishing process of the embodiment of the present invention, after the first detecting process, the chemical mechanical polishing process further comprises a step of performing a cleaning process by a nozzle initiated by a controller in the buffer region when the pre-polishing condition shows that a surface of a polished-to-be material layer of the wafer is abnormal.

According to the chemical mechanical polishing process of the embodiment of the present invention, the cleaning process includes a step of spraying deionized water, gas or chemical reagent.

According to the chemical mechanical polishing process of the embodiment of the present invention, after the first detecting process, the chemical mechanical polishing process further comprises a step of alarming to terminate the chemical mechanical polishing process by a controller in the buffer region when the pre-polishing condition shows that a polished-to-be material layer is not on the surface of the wafer.

According to the chemical mechanical polishing process of the embodiment of the present invention, after the second detecting process, the chemical mechanical polishing process comprises a step of moving the wafer back to the chemical mechanical polishing region by a controller in the buffer region when the post-polishing condition shows that there is remaining polished material on a surface of the wafer.

According to the chemical mechanical polishing process of the embodiment of the present invention, the wafer handling region controls a movement of the wafer within the chemical mechanical apparatus.

According to the chemical mechanical polishing process of the embodiment of the present invention, the wafer handling region possesses a plurality of robots for moving the wafer within the chemical mechanical polishing apparatus.

The present invention further provides a chemical mechanical polishing apparatus. The chemical mechanical polishing apparatus comprises a wafer handling region, a chemical mechanical polishing region and a buffer region. The wafer handling region possesses a plurality of robots.

According to the chemical mechanical polishing apparatus of the embodiment of the present invention, the buffer region is located at a path between the wafer handling region and the chemical mechanical polishing region.

According to the chemical mechanical polishing apparatus of the embodiment of the present invention, the detector comprises an optical detector.

According to the chemical mechanical polishing apparatus of the embodiment of the present invention, the optical detector includes a laser detector and an infrared detector.

According to the chemical mechanical polishing apparatus of the embodiment of the present invention, the buffer region comprises a controller and a nozzle and the controller controls the nozzle.

In the present invention, the chemical mechanical polishing apparatus equips a buffer region for performing the inspecting processes to insure whether there is peeling or damages on the wafer surface or whether the chemical mechanical polishing process is completely remove the polished-to-be material before the wafer is transported into the chemical mechanical polishing region or after the chemical mechanical polishing process is done on the wafer. Therefore, the chemical mechanical polishing region or other apparatus for later performing process can be prevent from being contaminated or damaged and the wafer can be prevent from damaged as well. Hence, the cost can be well controlled and the yield is increased.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

Figure 1:
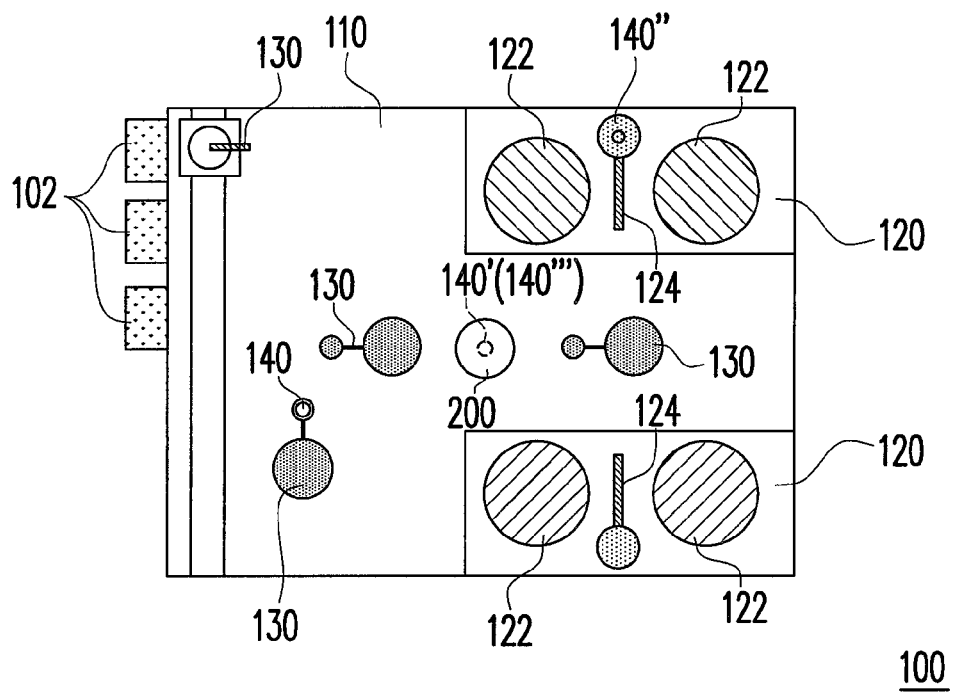
FIG. 1 is a top view schematically showing a chemical mechanical polishing apparatus according to a preferred embodiment of the invention.
Figure 2:
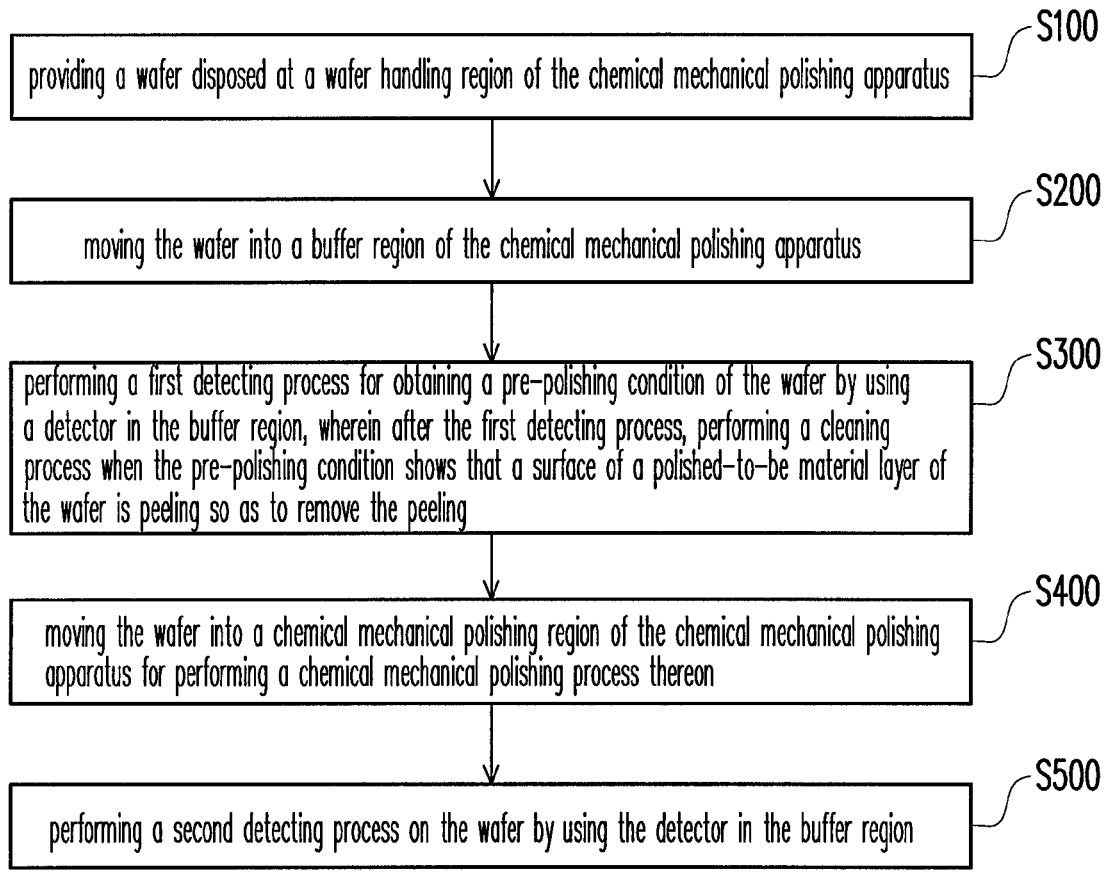
FIG. 2 is a flow chart illustrating an operating process for the chemical mechanical polishing apparatus according to one preferred embodiment of the invention.
Figure 3:
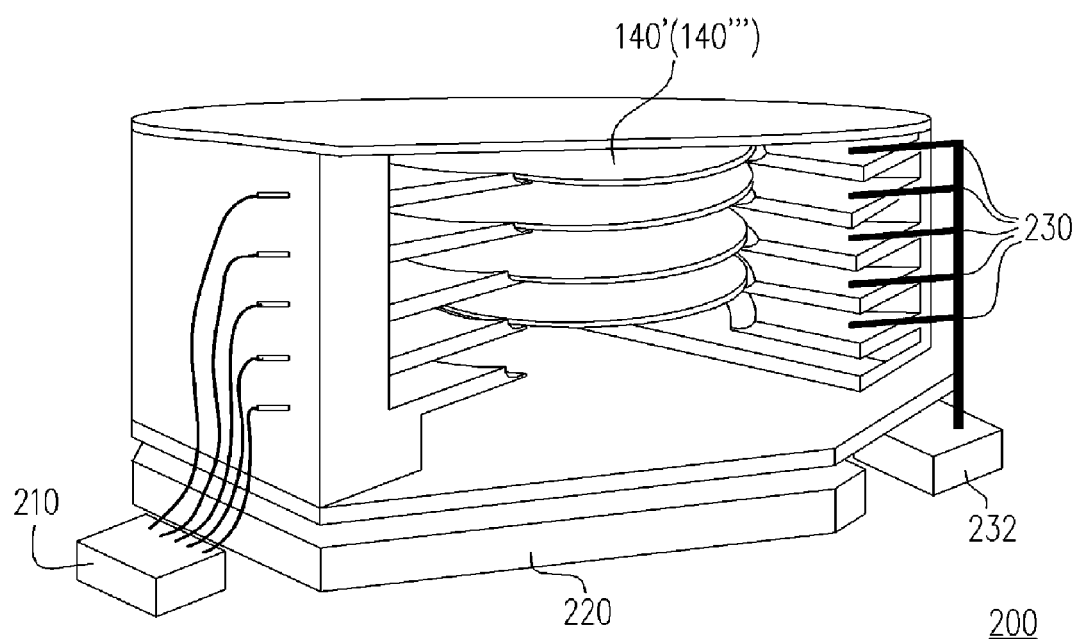
FIG. 3 is a cross-sectional view schematically showing a buffer region of a chemical mechanical polishing apparatus according to one preferred embodiment of the present invention.

FIG. 1 is a top view schematically showing a chemical mechanical polishing apparatus according to a preferred embodiment of the invention. FIG. 2 is a flow chart illustrating an operating process for the chemical mechanical polishing apparatus according to one preferred embodiment of the invention. FIG. 3 is a cross-sectional view schematically showing a buffer region of a chemical mechanical polishing apparatus according to one preferred embodiment of the present invention.

In FIG. 1, a chemical mechanical polishing apparatus 100 mainly comprises a wafer handling region 110, a chemical mechanical polishing region 120 and a buffer region 200. The regions mentioned above are responsible for the functionalities different from each other but are connected to each other, wherein the wafer handling region 110 predominates over the other regions within the chemical mechanical polishing apparatus and takes in charge of the polishing process performed on a wafer 140 within the chemical mechanical polishing apparatus 100. Further, the wafer handling region 110 equips several robots for moving the wafer 140. Additionally, the chemical mechanical polishing region 120 possesses several polishing platens 122. Furthermore, the chemical mechanical polishing apparatus 100 can perform different polishing process on wafers 140 in different polishing regions respectively. The detail process flow is described as following.

As shown in FIG. 1 and FIG. 2, in the step S100, a wafer 140 disposed at the wafer handling region 110 of the chemical mechanical polishing apparatus 100 is provided. The wafer handling region 110 takes in charge of moving and passing the wafer 140 into and out of the chemical mechanical polishing apparatus 100 so that the chemical mechanical polishing process can be correctly performed onto the wafer 140. The wafer handling region 110 can be, for example but not limited to, has several robots 130 for moving the wafer 140 to a position for performing the process. Furthermore, the chemical mechanical polishing apparatus 100 further comprises a wafer waiting region 102. After the manufacturing process such as chemical vapor deposition or other process is accomplished on the wafer 140 and before the wafer 140 is transported into the chemical mechanical polishing apparatus 100, the wafer 140 is passed into the wafer waiting region 102 to wait for being operated by the robot 130 of the wafer handling region 110.

Then, as shown in FIG. 1, together with FIG. 2 and FIG. 3, in the step S200, the wafer 140 is moved to the buffer region 200 of the chemical mechanical polishing apparatus 100 to be the wafer 140'. The buffer region 200 is depicted as FIG. 3. The buffer region 200 can be, for example but not limited to, comprise a detector 210, a controller 220 and a nozzle 230. Moreover, the buffer region 200 comprises a storage tank 232. The buffer region 200 can be, for example, a transport station located at the path between the wafer handling region 110 and the chemical mechanical polishing region 120. Before the wafer 140' is transported from the wafer handling region 110 into the chemical mechanical polishing region 120, the wafer 140' is moved into the buffer region 200. The detector 210 in the buffer region 200 is connected to the controller 220 and the controller 220 controls the nozzle 230 to spray liquid or gas in the storage tank 232 onto the wafer 140'.

It should be noticed that, in the conventional technology, the nozzle 230 spays deionized water onto the wafer to rinse the unpolished wafer 140'. If the wafer has a peeling surface, the peeling phenomenon will expand to the entire wafer when the wafer is washed or disregarded for a long time. Furthermore, if the wafer with a peeling surface is transported into later performed processes, such as the later performed chemical mechanical polishing process in the chemical mechanical polishing apparatus 120, the polishing apparatus will be contaminated and damaged even the wafer is damaged as well. Therefore, before the wafer 140' is polished, it is necessary to inspect whether there is peeling phenomenon on the wafer 140'. The inspection process is described as following.

As shown in FIG. 1, FIG. 2 and FIG. 3, in the step S300, a first detecting process is performed on the wafer 140' to obtain a pre-polishing condition of the wafer 140' by using the detector 210 in the buffer region 200. The detector 210 can be, for example but not limited to, optical detector such as laser detector or infrared detector. In the first detecting process, the detector 210 as described above receives the reflecting light from the wafer surface so as to determine whether there is cracks caused by peeling phenomenon is on the wafer, whether the conductive material layer or other polished-to-be material layer is deposited completely or whether the photoresist layer over the polished-to-be material layer is completely removed by analyzing the change of the wavelength, the change of the energy or the change of the reflection angle.

In one embodiment, when the pre-polishing condition mentioned above shows that the surface of the polished-to-be material layer on the wafer 140'is abnormal, in which there is peeling or damage on the surface of the wafer 140', the controller 220 in the buffer region 200 is initiated to turn on the nozzle 230 to perform a cleaning process. The cleaning process can be, for example, accomplished by spraying the deionized water, gas or chemical reagent in the storage tank 232 by the nozzle 230 onto the wafer 140' to clean the wafer 140' and remove the peeling.

In the other embodiment, when the pre-polishing condition shows that the color of the surface of the wafer 140' is abnormal, the controller 220 in the buffer region 200 also initiates to alarm so as to terminate the chemical mechanical polishing process in the chemical mechanical polishing apparatus 100. The reasons lead to abnormal color of the surface of the wafer 140' can be that there is no polished-to-be material layer on the top surface of the wafer 140' or there is photoresist layer remaining on the top surface of the wafer 140'. Once the wafer 140' with abnormal wafer surface as described above is transported into the chemical mechanical polishing region 120 to perform a chemical mechanical polishing process thereon, it is highly possible that the wafer is damaged and the chemical mechanical polishing apparatus 100 is contaminated.

Most importantly, the first detecting process is not limited to using optical detector to detect cracks on the wafer surface or the color of the wafer surface. That is, when there exists possible damages on the wafer 140', the detector with different design layout can be also used to determine whether the wafer 140' can be put into further process steps.

The detector 210 in the buffer region 200 can check the wafer 140' before the wafer 140' is moved into the chemical mechanical polishing region 120 so as to prevent the chemical mechanical polishing region 120 from being damaged by a wafer with a peeling surface or other surface defects. Therefore, the chemical mechanical polishing region 120 can be prevented from being contaminated and the wafer can be prevent from being damaged. Hence, the cost can be well controlled and the yield is increased.

When the wafer 140' with peeling surface or defects is recovered or removed or is passed the first detecting process, the following steps can be performed.

Thereafter, as shown in FIG. 1 and FIG. 2, in the step S400, the wafer 140' is moved into the chemical mechanical polishing region 120 of the chemical mechanical polishing apparatus 100 to be a wafer 140". A chemical mechanical polishing process is performed on the wafer 140". There are several polishing platens 122 and robots 124 in the chemical mechanical polishing region 120 for performing the chemical mechanical polishing process. Since the chemical mechanical polishing process is well known in the art, it is not necessary to detail described herein.

Thereafter, as shown in FIG. 1 and FIG. 2, in the step S500, the wafer 140" is moved into the buffer region 200 to be a wafer 140'''.

Then, as shown in FIG. 1 together with FIG. 2 and FIG. 3, in the step S600, a second detecting process is performed on the wafer 140''' to obtain a post-polishing condition of the wafer by using the detector 210 in the buffer region 200.

In one embodiment, when the post-polishing condition shows that there is material remaining on the wafer surface, in which the polished-to-be material layer still remains on the surface of the wafer 140''', the controller 210 in the buffer region 200 transports the wafer 140''' back to the chemical mechanical polishing region 120 so as to re-perform the chemical mechanical polishing process.

In the buffer region 200, the wafer 140''' is inspected to insure that whether the polished-to-be material layer is completely removed so as to avoid the wafer having the polished-to-be material residue thereon passing into the next manufacturing process to contaminate or damage other apparatus or to damage the wafer 140'''.

It should be noticed that the chemical mechanical polishing apparatus 100 and the buffer region 200 are not limited to the structures shown in FIG. 1 and FIG. 3. The structures of the chemical mechanical polishing apparatus 100 and the buffer region 200 can be designed to comply with different apparatus. The buffer region 200 can be also comply with different chemical mechanical apparatus and the location and the structure of the buffer region within the chemical mechanical apparatus is not limited to the description mentioned above.

Altogether, before the wafer is transported into the chemical mechanical polishing region or after the chemical mechanical polishing process is done on the wafer, the detector in the buffer region takes in charge of the inspecting process to insure whether there is peeling or damages on the wafer surface or whether the chemical mechanical polishing process is completely remove the polished-to-be material. Therefore, the chemical mechanical polishing region or other apparatus for later performing process can be prevent from being contaminated or damaged and the wafer can be prevent from damaged as well. Hence, the cost can be well controlled and the yield is increased.

It will be apparent to those skilled in the art that various modifications and variations can be made to the structure of the present invention without departing from the scope or spirit of the invention. In view of the foregoing descriptions, it is intended that the present invention covers modifications and variations of this invention if they fall within the scope of the following claims and their equivalents.

What is claimed is:

1. A chemical mechanical polishing process, comprising:
providing a wafer disposed at a wafer handling region of a chemical mechanical polishing apparatus;
moving the wafer into a buffer region of the chemical mechanical polishing apparatus;
performing a first detecting process for obtaining a pre-polishing condition of the wafer by using a detector in the buffer region, wherein after the first detecting process, performing a cleaning process when the pre-polishing condition shows that a surface of a polished-to-be material layer of the wafer is peeling so as to remove the peeling;
moving the wafer into a chemical mechanical polishing region and performing a chemical mechanical process; and
performing a second detecting process, in the buffer region, for obtaining a post-polishing condition of the wafer by using the detector of the buffer region.

2. The chemical mechanical polishing process of claim 1, the detector includes an optical detector.

3. The chemical mechanical polishing process of claim 2, wherein the optical detector includes a laser detector and an infrared detector.

4. The chemical mechanical polishing process of claim 1, wherein the cleaning process includes a step of spraying deionized water, gas or chemical reagent.

5. The chemical mechanical polishing process of claim 1, after the first detecting process, further comprising alarming to terminate the chemical mechanical polishing process by a controller in the buffer region when the pre-polishing condition shows that a polished-to-be material layer is not on the surface of the wafer.

6. The chemical mechanical polishing process of claim 1, after the second detecting process, further comprising moving the wafer back to the chemical mechanical polishing region by a controller in the buffer region when the post-polishing condition shows that there is remaining polished material on a surface of the wafer.

7. The chemical mechanical polishing process of claim 1, wherein the wafer handling region controls a movement of the wafer within the chemical mechanical apparatus.

8. The chemical mechanical polishing process of claim 1, wherein the wafer handling region possesses a plurality of robots for moving the wafer within the chemical mechanical polishing apparatus.

* * * * *